United States Patent [19]

Winkley et al.

[11] 4,003,888

[45] Jan. 18, 1977

[54] AMINOALKYL ETHERS OF 2- AND 3-HYDROXYBENZIL

[75] Inventors: Michael W. Winkley, Malvern; Gerhard R. Wendt, Havertown, both of Pa.

[73] Assignee: American Home Products Corporation, New York, N.Y.

[22] Filed: Oct. 30, 1975

[21] Appl. No.: 627,488

[52] U.S. Cl. .................. 260/239 B; 260/293.73; 260/239 BF; 260/293.8; 260/326.5 S; 260/326.5 A; 260/326.5 J; 260/570.7; 424/244; 424/267; 424/274; 424/330; 424/199

[51] Int. Cl.² .................................. C07D 295/08

[58] Field of Search ... 260/239 B, 239 BF, 326.5 J, 260/326.5 A, 326.5 S, 293.8, 293.73

[56] References Cited

UNITED STATES PATENTS

| 2,681,340 | 6/1954 | Ehrhart | 260/293.8 |
|---|---|---|---|
| 3,077,472 | 2/1963 | Burckhalter | 260/239 B |

FOREIGN PATENTS OR APPLICATIONS

| 164,700 | 8/1955 | Australia | 260/293.8 |
|---|---|---|---|
| 40-27177 | 11/1965 | Japan | 260/293.8 |

Primary Examiner—Alton D. Rollins
Assistant Examiner—Mack L. Berch
Attorney, Agent, or Firm—David E. Frankhouser

[57] ABSTRACT

Dialkylaminoalkyl ethers of 2- and 3-hydroxybenzil are prepared by reacting the thallium salt of 2- or 3-hydroxybenzil with a dialkylaminoalkylchloride. The products have antiarrhythmic activity.

2 Claims, No Drawings

AMINOALKYL ETHERS OF 2- AND 3-HYDROXYBENZIL

This invention relates to chemical compounds classified in the art of organic chemistry as aminoalkylethers of 2- and 3-hydroxybenzil having useful pharmacological activity. The compound 5,5'-dichloro-2,3'-bis(2-diethylaminoethoxy)benzil is described by J. Finkelstein and S. M. Linder, J. Amer. Chem. Soc., 71, 1010 (1949).

The invention sought to be patented comprises compounds having the molecular formula:

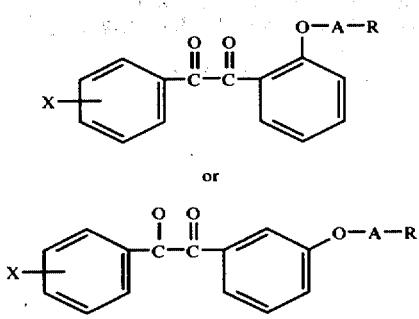

wherein X is hydrogen, lower alkyl, lower alkoxy, halo, or nitro; A is a divalent aliphatic hydrocarbon radical of the formula

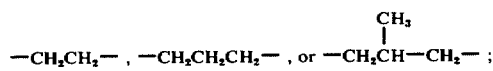

and R is a substituted amino group of the formula

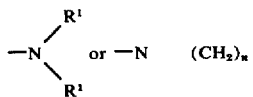

wherein $R^1$ is methyl, ethyl, propyl, or isopropyl, and $n$ is the number 4, 5, 6, 7, or 8; and the non-toxic, pharmaceutically acceptable acid addition salts thereof. Compounds of Formula I or II where X is hydrogen are preferred.

The compounds of Formula I and II in standard pharmacological test procedures elevate the electrical fibrillatory threshold of anesthetized dogs evidencing usefulness as antiarrhythmic agents.

The compounds of Formula I and II are prepared by condensing a thallium salt of a 2-hydroxybenzil or a 3-hydroxybenzil with an appropriate di(substituted-)aminoalkyl chloride in refluxing toluene or toluene-dimethylformamide. The compounds obtained in the free base form can be conveniently isolated and purified in the form of an acid addition salt. Such salts are made by conventional methods such as by combining the base and a suitable acid in a reaction-inert organic solvent.

The thallium salts are prepared by reaction of 2-hydroxybenzil or 3-hydroxybenzil with thallium (I) ethoxide in an inert organic solvent, for example benzene, toluene, or ethanol-benzene. Soluble salts can be used in situ or, if a precipitate forms, it can be isolated by filtration. [See Taylor et al., J. Am. Chem. Soc., 90, 245 (1968) and Paquet et al., Can. J. Chem., 51, 3855 (1973)].

For pharmacological purposes the compounds can be employed in the form of acid addition salts with non-toxic and pharmaceutically acceptable acids. Such acids will be apparent to one skilled in the art. Appropriate salts are those formed from either inorganic or organic acids, for example hydrochloric, hydrobromic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic, benzenesulfonic, p-toluenesulfonic, and 2-naphthalenesulfonic.

As used herein and in the claims the terms "lower alkyl" and "lower alkoxy" refer to groups containing from one to four carbons. The term "halo" means fluoro, chloro, bromo, or iodo.

The methods of making and using the compounds of the invention are illustrated in the following examples:

EXAMPLE I

1-[2-[2-(Hexahydro-1H-azepin-1-yl)-ethoxy]phenyl]-2-phenylethanedione

Thallous ethoxide (2.5 g.) in toluene (50 ml.) was added to 2-hydroxybenzil (2.3 g.) [prepared by the method of K. Brass, E. Willing and R. Hanssen, Ber., 63, 2613 (1930)] and the mixture was distilled with a small Dean-Stark trap. To the resulting solution was added 12 ml. of a solution (80 g. per 500 ml.) of 2-(hexamethylimino)ethyl chloride in toluene. The mixture was stirred and heated under reflux for 20 minutes. After cooling the precipitate was collected and washed with toluene. The filtrate and washings were evaporated to a syrup which was further evaporated under oil pump vacuum. The syrup was dissolved in ether and a solution of hydrogen chloride in ether was added. The resulting precipitate was collected and crystallized from methanol-ether to give 2.11 g. of crude product, m.p. 181°–183°. Recrystallization gave pure title product as the hydrochloride, m.p. 182°–185°.

Analysis for: $C_{22}H_{26}ClNO_3$
Calculated: C, 68.12; H, 6.76; Cl, 9.14; N, 3.61
Found: C, 67.87; H, 6.82; Cl, 9.06; N, 3.32

Example II

The antiarrhythmic activity of the compounds of the invention is demonstrated and ellicited by the following test method:

The heart of an anesthetized dog is exposed by a left thoractomy. Bipolar electrodes are sutured to the epicardial surface of the left ventricle. The heart is stimulated with square wave pulses of 3 msec. duration and frequency of 60 Hz. for periods of 5 sec. Voltage is increased until fibrillation ensues. The heart is then defibrillated by DC countershock and the procedure repeated at 10 min. intervals. Drugs are administered i.v. over periods of 3 min. and fibrillatory threshold examined 10 min. after start of injection of each dose. Effective antiarrhythmic agents elevate the fibrillatory threshold.

When tested as set forth above the compound of Example I elevates the electrical fibrillatory threshold at a dose of 10 mg/kg. body weight.

What is claimed is:
1. A compound of the formula:

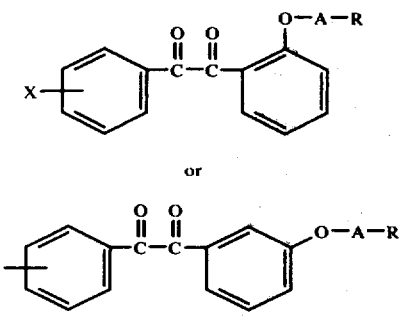

wherein A is a divalent aliphatic hydrocarbon radical of the formula

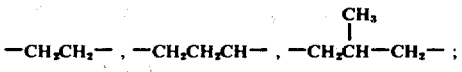

and R is a substituted amino group of the formula

wherein X is hydrogen, lower alkyl, lower alkoxy, halo, or nitro; and $n$ is the number 4, 5, 6, 7, or 8; and the non-toxic, pharmaceutically acceptable acid addition salts thereof.

2. A compound as defined in claim 1 which is 1-[2-[2-(hexahydro-1H-azepin-1-yl)ethoxy]phenyl]-2-phenylethanedione.

* * * * *